US00PP27872P3

(12) United States Plant Patent
Juneau

(10) Patent No.: US PP27,872 P3
(45) Date of Patent: Apr. 11, 2017

(54) GRAPE PLANT NAMED 'CHENIBEC'

(50) Latin Name: ***Vitis* hybrid**
Varietal Denomination: Chenibec

(71) Applicant: Ronald Juneau, Pont-Rouge (CA)

(72) Inventor: Ronald Juneau, Pont-Rouge (CA)

( * ) Notice: Subject to any disclaimer, the term of this patent is extended or adjusted under 35 U.S.C. 154(b) by 0 days.

(21) Appl. No.: 14/545,919

(22) Filed: Jul. 8, 2015

(65) Prior Publication Data

US 2016/0014942 P1 Jan. 14, 2016

(30) Foreign Application Priority Data

Jul. 11, 2014 (CA) ..... 14-8384

(51) Int. Cl.
*A01H 5/08* (2006.01)

(52) U.S. Cl.
USPC ..... Plt./207

(58) Field of Classification Search
USPC ..... Plt./207
See application file for complete search history.

*Primary Examiner* — Annette Para
(74) *Attorney, Agent, or Firm* — Penny J. Aguirre

(57) ABSTRACT

A new cultivar of grape plant named, 'Chenibec', that is characterized by its open and even plant habit, its fruit that is large in size and golden in color at maturity, its juicy berries with a crisp, fruity, wine-like taste, its large, shouldered, medium density fruit clusters that are full of berries, its vigorous growth rate and high level of fruit productivity, and its grapes that are suitable for secondary fermentation to produce sparkling and champagne style wine.

2 Drawing Sheets

Botanical classification: *Vitis* hybrid.
Cultivar designation: 'Chenibec'.

BACKGROUND OF THE INVENTION

The present invention relates to a new and distinct cultivar of *Vitis* hybrid named 'Chenibec' and will be hereafter referred to by its cultivar name 'Chenibec'. 'Chenibec' represents a new cultivar of grape grown for fruit and wine production.

The new cultivar was derived from a controlled breeding program conducted by the Inventor in Portneuf, Québec, Canada. The objective of the breeding program is to develop new cold hardy grape varieties with good winemaking characteristics.

'Chenibec' resulted from a cross made in 1990 between the *Vitis* hybrid cultivar Elmer Swenson 'E.S. 2-3-17' (not patented) as the female parent and the *Vitis vinifera* cultivar 'Chenin blanc' (not patented) as the male parent. The Inventor selected 'Chenibec', in 1998 as a single unique plant from amongst the resulting seedlings.

Asexual propagation of the new cultivar was first accomplished by the Inventor by hardwood stem cuttings in 2000 in Saint-Ubalde, Québec, Canada. Asexual propagation by hardwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Chenibec' as a new and unique cultivar of grape.

1. 'Chenibec' exhibits an open and even plant habit.
2. 'Chenibec' exhibit fruit that is large in size and golden in color at maturity.

3. 'Chenibec' exhibits juicy berries with a crisp, fruity, wine-like taste.
4. 'Chenibec' exhibits large, shouldered, medium density fruit clusters that are full of berries.
5. 'Chenibec' exhibits a vigorous growth rate and a high level of fruit productivity.
6. 'Chenibec' exhibits grapes suitable for secondary fermentation to produce sparkling and champagne style wine.

The female parent of 'Chenibec', 'E.S. 2-3-17' differs from 'Chenibec' in having a less vigorous growth habit, in having smaller, lighter fruit clusters, in having berries that are smaller in size, and in having differently shaped leaves. The male parent of 'Chenibec', 'Chenin blanc' differs from 'Chenibec' in being less winter hardy, in being more susceptible to disease, and in having berries that are smaller in size and more acidic in taste. 'Chenibec' can be most closely compared to the *Vitis* cultivars 'Adalmiina' (not patented) and 'Louise Swenson' (not patented). 'Adalmiina' is similar to 'Chenibec' in being suitable for the production of sparkling wine and in having grapes that are golden in color at maturity. 'Adalmiina' differs from 'Chenibec' in having less dense fruit clusters that are cylindrical in shape, in having berries that are smaller in size, in having ovate shaped leaves with shallow lobes, and in being suitable for the production of French Muscadet style wine. 'Louise Swenson' is similar to 'Chenibec' in being suitable for the production of sparkling wine. 'Louise Swenson' differs from 'Chenibec' in having smaller fruit clusters that do not have a shoulder, in having less dense fruit clusters, and in being suitable for the production of white burgundy style wine.

BRIEF DESCRIPTION OF THE DRAWINGS

The accompanying colored photographs illustrate the overall appearance and distinct characteristics of the new grape cultivar. The photographs were taken of eight year-old plants of the new cultivar as grown outdoors in a field in Saint-Ubalde, Québec, Canada.

The photograph in FIG. 1 provides a side view of the plant habit of 'Chenibec' with fruit clusters.

Figure 1:
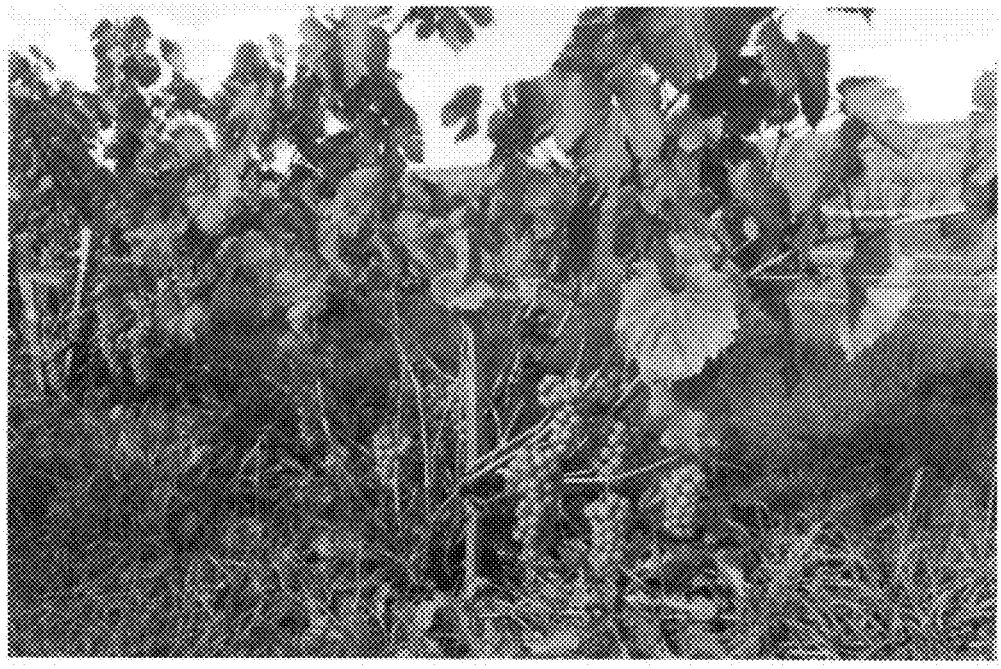
Figure 2:
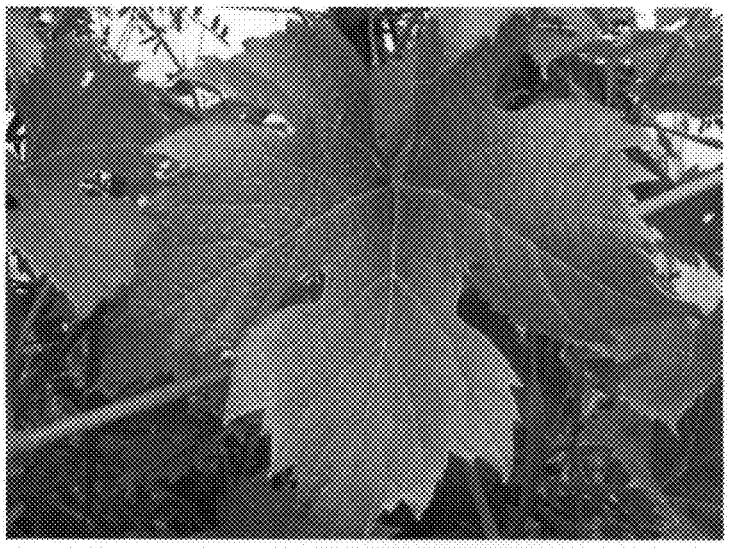

The photograph in FIG. 2 provides a close-up view of the foliage of 'Chenibec'.

Figure 3:
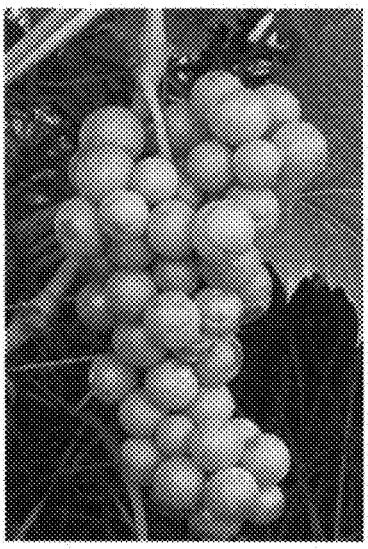

The photograph in FIG. 3 provides a close-up view of the immature fruit of 'Chenibec'.

Figure 4:
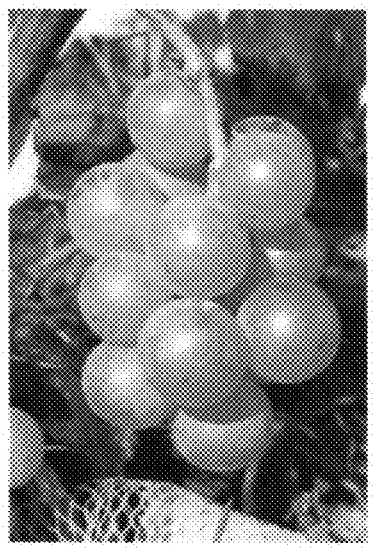

The photograph in FIG. 4 provides a close-up view of the ripening fruit of 'Chenibec'.

The colors in the photographs are as close as possible with digital photography techniques available, the color values cited in the detailed botanical description accurately describe the colors of the new cultivar of grape.

DETAILED BOTANICAL DESCRIPTION OF THE PLANT

The following is a detailed description of plants seven years in age as grown outdoors in a trial field in Saint-Ubalde, Québec, Canada. The phenotype of the new cultivar may vary with variations in environmental, climatic, and cultural conditions, as it has not been tested under all possible environmental conditions. The color determination is in accordance with The 2001 R.H.S. Colour Chart of The Royal Horticultural Society, London, England, except where general color terms of ordinary dictionary significance are used.

General description:

*Blooming period.*—Mid to late June in Québec, Canada.

*Plant type.*—Perennial fruit producing vine.

*Plant habit.*—Open, vase-shaped, and spreading.

*Height and spread.*—An average of 1.2 m in height and 220 cm in width.

*Cold hardiness.*—At least to U.S.D.A. Zone 3 (with snow cover).

*Diseases and pests.*—Resistance to downy mildew (*Plasmopara viticola*), powdery mildew (*Uncinula necator*), and black rot (*Guignardia bidwellii*).

*Propagation.*—Hardwood cuttings (preferred) and stem cuttings.

*Root description.*—Fibrous and fine, 198D in color.

*Root development.*—An average of 21 days for root initiation with a rooted cutting produced after an average of 53 days.

*Growth rate.*—Vigorous.

Stem description:

*Branching habit.*—Pruned to have four dormant main stems per trunk, with an average of 6 primary canes per dormant stem (an average of 23 primary canes per plant).

*Stem size.*—Primary canes; an average of 114.9 cm in length and 8 mm in diameter, dormant stems; and average of 18.25 cm in length and 10 mm in diameter, trunk; and average of 5 cm in length and 20 mm in diameter.

*Stem shape.*—Rounded with longitudinal striations.

*Stem strength.*—Medium.

*Stem aspect.*—Upright to horizontal.

*Stem surface.*—Smooth and slightly striated.

*Stem color.*—Growing shoots; 144A, mature canes; sun exposed surface; 178B and shade exposed surface; a blend between 144A and 146B.

*Internode length.*—An average of 13.25 cm on mature canes.

*Stem tendrils.*—Present, pattern 1, 2, etc., an average of 23.9 cm in length, 146B to 146C in color.

*Bud.*—Axillary buds are 3 mm in length and 2 mm in width, 144B lightly suffused with 178B in color.

Foliage description:

*Leaf shape.*—Ovate with an average of 3 to 5 lobes.

*Leaf division.*—Simple.

*Leaf base.*—Cordate to auriculate.

*Leaf apex.*—Acute.

*Leaf venation.*—Palmate overall and pinnate within lobes, color; upper surface 145B and lower surface 146C, average lengths of main veins (taken from pressed mature leaves); N1 13.73 cm, N2 12.15 cm, N3 10.20 cm, N4 4.45 cm, N5 1.2 cm.

*Leaf margins.*—3 to 5 lobed with lobe margins serrate.

*Leaf attachment.*—Petiolate.

*Leaf arrangement.*—Alternate.

*Leaf surface.*—Both surfaces smooth, lower surface; sparsely pubescent mainly on veins.

*Leaf color.*—Young upper surface 144A and lower surface 146C, mature upper surface 146A and lower surface 146B.

*Leaf size.*—An average of 17.7 cm in length and 17.0 cm in width.

*Leaf quantity.*—An average of 9 per cane.

*Petioles.*—Round in shape, an average of 10 cm in length and 4.5 mm in width, color; sun exposed surface 183B to 183C and shade exposed surface 146B to 146C, surface; smooth and sparsely pubescent, petiole sinus is very open, u-shaped, and an average of 4.58 cm in depth and 3.6 cm in width.

Inflorescence description:

*Inflorescence type.*—Narrow panicle of drooping to pendulant flowers, conical in shape, wider at the shoulder.

*Inflorescence quantity.*—An average of 2 to 3 per primary cane.

*Inflorescence size.*—An average of 10.2 cm in length and 5 cm in width (at the shoulder).

*Lastingness of inflorescence.*—An average of 5 days, self-cleaning.

*Fragrance.*—Spicy scent.

*Flowers.*—Perfect, campanulate, an average of 173 flowers per panicle.

*Flower buds.*—Rounded to globular in shape, an average of 3 mm in length and diameter, a blend between 144B and N144C in color.

*Flower size.*—An average of 5.5 mm in length and 5 mm in width.

*Calyx.*—5 sepals fused into a flattened cup less than 1 mm in length and width, entire margin, apex fused to ovary, base fused to pedicel, color; upper and lower surface a blend of 144B and N144C surface texture glabrous on both surfaces.

*Petals.*—5, fused into the campanulate shaped calyptra (cap), entire margin, fused apex, reflexed base, an average of 2.5 mm in length and 1 mm in width, color when opening and when fully open upper and lower surface; a blend between 144B and N144C, upper and lower surface texture; smooth.

*Pedicels.*—Rounded in shape, an average of 2 mm in length and less than 1 mm in diameter, 144B in color, surface texture glabrous.

*Peduncles.*—Rounded in shape, an average of 3.2 cm in length and 3.2 mm in diameter (from stem to base of inflorescence), 144B with shading of 183B on sun upper surface in color, surface texture sparsely pubescent.

Reproductive organs:

*Androecium.*—An average of 5 stamens, anthers; kidney shaped, 4D in color, an average of 1 mm in length, filaments; an average of 5 mm in length and <1 mm in width, 157A in color, pollen is moderate in quantity and 4D in color.

*Gynoecium.*—1 pistil, style; 143B in color, stigma; circular in shape, 143B in color, ovary; superior, 2 mm in length and width, and 143B in color.

Fruit description:

*Fruit cluster number.*—An average of 14 per plant.

*Fruit yield.*—An average of 1.5 kg per plant in Saint-Ubalde and Pont-Rouge, Canada on seven year-old plants.

*Fruit set.*—Moderate, 80%.

*Fruit cluster size.*—Medium to medium-large, an average of 8 cm in diameter and 14.7 cm in height.

*Fruit cluster shape.*—Conical to conical winged, with shoulder present.

*Fruit weight.*—An average of 2.5 g per berry.

*Fruit chemistry* .—Averages: brix 21.92, % tritratable acidity 0.77.

*Harvest date.*—The first and second weeks of October.

*Position of maximum berry diameter.*—Midway between proximal and distal ends.

*Berry shape.*—Globose.

*Berry symmetry.*—Symmetric.

*Persistence of calyx.*—Persistent at harvest, 177B in color, an average of 2 mm in length.

*Berry surface.*—Smooth.

*Waxiness of skin.*—Slightly glaucescent.

*Thickness of skin.*—Thin.

*Skin color.*—Immature 144A, maturing 144A to 144B heavily suffused with 152B, mature a blend of 152B to 152D and 153B.

*Color of flesh.*—A blend of 152D and 153D in color.

*Fruit maturity date.*—Ripen at an average of 1050 growing degree days.

*Seed.*—Rectangular-ovoid in shape, an average of 2.5 per berry, an average of 5.75 mm in length and 4.25 mm in diameter, a blend of 160D and 161D in color when fresh, dries to 165A to 165C in color.

*Berry firmness* (*without skin*).—Moderate.

*Texture of flesh.*—Pulpy, juicy.

*Flavor.*—Crisp, light, fruity, fragrant.

*Fruit use.*—Production of high quality sparkling and champagne style wines.

*Wine quality.*—Sparkling white and champagne style, crisp, fruity flavors and aromas, light and fragrant body, 16D in color, overall high quality.

It is claimed:

1. A new and distinct cultivar of Grape plant named 'Chenibec' as herein illustrated and described.

* * * * *